United States Patent [19]

Kalthoff et al.

[11] 4,418,563
[45] Dec. 6, 1983

[54] METHOD OF DETERMINING THE IMPACT FRACTURE TOUGHNESS $K_{ID}$ BY MEANS OF IMPACT TESTS

[75] Inventors: Jörg F. Kalthoff, Bad-Krotzingen; Siegfried Winkler, Freiburg, both of Fed. Rep. of Germany

[73] Assignee: Fraunhofer-Gesellschaft zur Förderung der angewandten Forschung, Munich, Fed. Rep. of Germany

[21] Appl. No.: 321,144

[22] Filed: Nov. 13, 1981

[30] Foreign Application Priority Data

Nov. 28, 1980 [DE] Fed. Rep. of Germany ....... 3044841

[51] Int. Cl.$^3$ .............................................. G01N 3/08
[52] U.S. Cl. ........................................ 73/12; 73/799; 73/844
[58] Field of Search ............................ 73/844, 799, 12

[56] References Cited

U.S. PATENT DOCUMENTS 3,513,687 5/1970 Griffin et al. .......................... 73/844
3,583,215 6/1971 Franz .................................... 73/844
4,085,609 4/1978 Kelly .................................... 73/844

OTHER PUBLICATIONS

Ireland, D. R. (1976), "Critical Review of Instrumented Impact Testing", Proc. Int. Conf. Dynamic Fracture Toughness, London.
Glover, A. P., F. A. Johnson, J. C. Radon and C. E. Turner (1976), "Dynamic Fracture Toughness Measurement by Instrumented Impact Bend Testing and Compact K Testing", Proc. Int. Conf. Dynamic Fracture Toughness, London.
Winkler, S., J. F. Kalthoff and A. Gerscha (1979), "The Response of Pressure Vessel Steel Specimens on Drop Weight Loading", Proc. 5th Int. Conf. on Structure Mechanics in Reactor Technology, Berlin, vol. G (4/6), North-Holland Publishing Company.
IIW (International Institute of Welding, Commission X), U.K. Briefing Group on Dynamic Testing (1976) "Some Porposals for Dynamic Toughness Measurement", Proc. Int. Conf. Dynamic Fracture Toughness, London.
Kalthoff, J. F., J. Beinert, and S. Winkler (1977), "Measurements of Dynamic Sress Intensity Factors for Fast Running and Arresting Cracks in Double-Cantilever-Beam Specimens", ASTM STP 627-*East Fracture and Crack Arrest*, American Society for Testing and Materials, Philadelphia, pp. 161-176.

*Primary Examiner*—Howard A. Birmiel
*Attorney, Agent, or Firm*—John C. Smith, Jr.

[57] ABSTRACT

A method of determining the impact fracture toughness $K_{id}$ of construction materials, for example structural steels or plastic materials, without the need of performing a load measurement at the striking hammer is provided. The elastic response of the specimen to the impact process, i.e. the dynamic stress intensity factor versus time curve, $K_I^{dyn}(t)$, is determined in pre-experiments. The shadow optical method of caustics in reflection with an appropriate high strength steel is utilized for establishing this impact response curve. The dynamic fracture toughness for a given constructional material is then determined by performing an impact experiment and measuring the time to fracture $t_f$. $K_{Id}$ is obtained from the measured $t_f$-value and the pre-established impact response curve which corresponds to the experimental test conditions. The presented measuring procedure is used for determining the dynamic fracture toughness of two different steels at different test temperatures.

6 Claims, 7 Drawing Figures

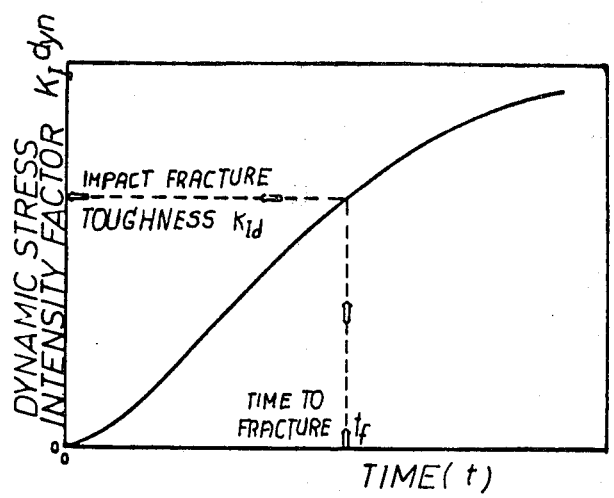
FIG. 1
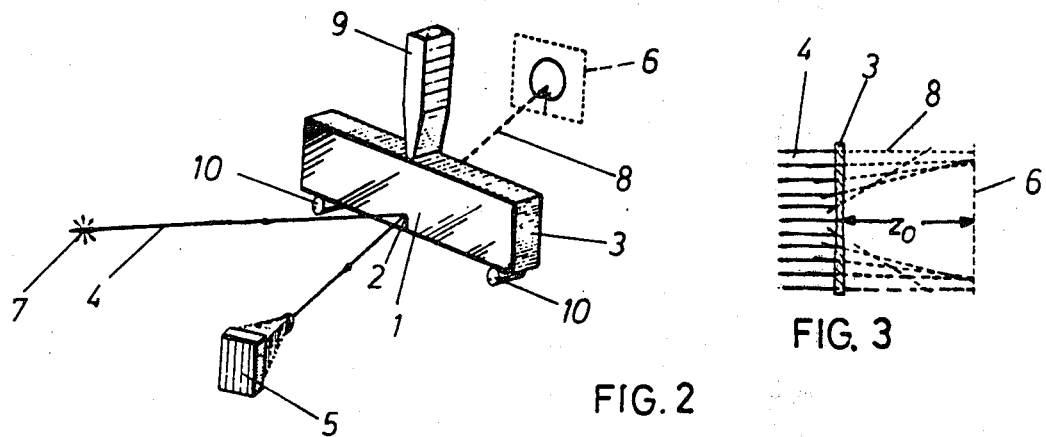
FIG. 2
FIG. 3
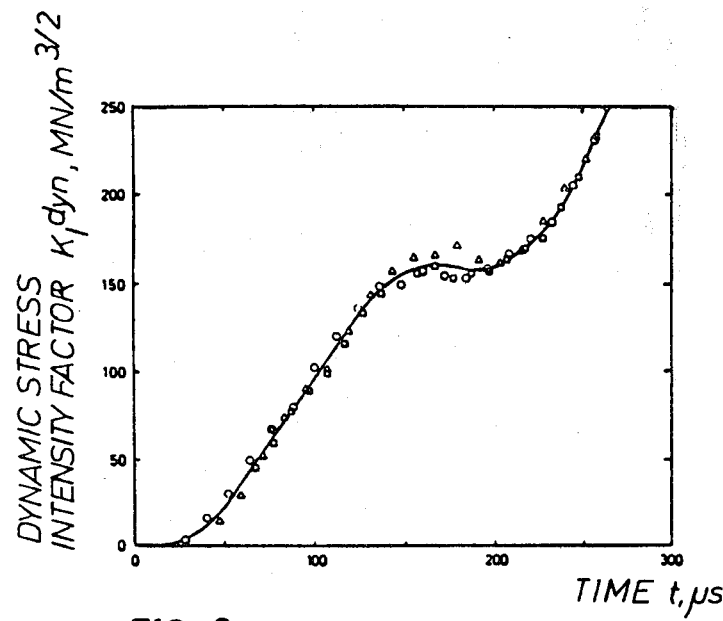
FIG. 6

METHOD OF DETERMINING THE IMPACT FRACTURE TOUGHNESS $K_{ID}$ BY MEANS OF IMPACT TESTS

BACKGROUND OF THE INVENTION

Instrumented impact tests are currently used to measure the dynamic fracture toughness $K_{Id}$ of materials. During the impact event, the load at the peen of the striking hammer is measured as a function of time or deflection of the specimen. From the critical load for onset of crack propagation the dynamic fracture toughness value $K_{Id}$ is derived utilizing the conventional static stress intensity factor formulas (ASTM STP 466 (1970)—*Impact Testing of Metals*, American Society for Testing and Materials, Philadelphia; ASTM STP 563 (1974)—*Instrumented Impact Testing*, American Society for Testing and Materials, Philadelphia; IIW (International Institute of Welding, Commission X), U.K. Briefing Group on Dynamic Testing (1976), "Some Proposals for Dynamic Toughness Measurement," Proc. Int. Conf. Dynamic Fracture Toughness, London; PVRC/MPC Joint Task Group on Fracture Toughness Properties for Nuclear Components, Working Group on Instrumented Precracked Charpy Test, Chairman C. Buchalet, Westinghouse Nuclear Energy Systems (1974), "Recommended Procedure for Instrumented Precracked Charpy Testing").

However, difficulties are inherent with this measuring and evaluation procedure: first, because the load time records oscillate and often cause uncertainties in the determination of the actual fracture load, and secondly, because a dynamic material strength value $K_{Id}$ is inferred from a static evaluation analysis.

The conventional measuring technique therefore can only yield meaningful data if fracture occurs only after time sufficiently long that a quasi static loading condition has been reached in the specimen. For shorter loading times to fracture dynamic effects can strongly influence the stress state in the specimen (Glover, A. P., F. A. Johnson, J. C. Radon and C. E. Turner (1976), "Dynamic Fracture Toughness Measurement by Instrumented Bend Testing and Compact K Testing," Proc. Int. Conf. Dynamic Fracture Toughness; Kalthoff, J. F., S. Winkler, and J. Beinert (1979), "The Influence of Dynamic Effects in Impact Testing," *Int. Journ. of Fracture*, 13, pp. 528–531; Ireland, D. R. (1976), "Critical Review of Instrumented Impact Testing," Proc. Int. Conf. Dynamic Fracture Toughness, London; Loss, J. F., J. R. Hawthorne, and C. A. Griffis (1975), "Fracture Toughness of Light Water Reactor Pressure Vessel Materials," Naval Research Laboratory Memorandum Report 3036; Radon, J. C., and C. E. Turner (1969), "Fracture Toughness Measurements By Instrumented Impact Test," *J. Engng. Frac. Mech.*, Vol. 1, No. 3, p. 165; Turner, C. E. (1970), "Measurement of Fracture Toughness by Instrumented Impact Test"; ASTM STP 466—*Impact Testing of Metals*, American Society for Testing and Materials, Philadelphia, pp. 93–114; Venzi, S., A. H. Priest, and J. J. May (1970), "Influence of Inertial Load in Instrumented Impact Tests;" ASTM STP 466—*Impact Testing of Metals*, American Society for Testing and Materials, Philadelphia, pp. 165–180; Winkler, S., J. F. Kalthoff, and A. Gerscha (1979), "The Response of Pressure Vessel Steel Specimens on Drop Weight Loading," Proc. 5th Int. Conf. on Structural Mechanics in Reactor Technology, Berlin, Vol. G(4/6), North-Holland Publishing Company). If these dynamic influences on the measured load records are not taken into account, erroneous data can be obtained which may lead to an overestimation of the true toughness of the material (IIW (International Institute of Welding, Commission X), U.K. Briefing Group on Dynamic Testing (1976), "Some Proposals for Dynamic Toughness Measurement," Proc. Int. Conf. Dynamic Fracture Toughness, London; Glover, A. P., F. A. Johnson, J. C. Radon, and C. E. Turner (1976), "Dynamic Fracture Toughness Measurement by Instrumented Bend Testing and Compact K Testing," Proc. Int. Conf. Dynamic Fracture Toughness, London; Matthews, W. T. (1970), "The Role of Impact Testing in Characterizing the Toughness of Materials," ASTM STP 466—*Impact Testing of Metals*, American Society for Testing and Materials, Philadelphia, pp. 3–20; Turner, C. E. (1970), "Measurement of Fracture Toughness by Instrumented Impact Test," ASTM STP 466—*Impact Testing of Metals*, American Society for Testing and Materials, Philadelphia, pp. 93–114. It is postulated, therefore (Ireland, D. R. (1976)), "Critical Review of Instrumented Impact Testing," Proc. Int. Conf. Dynamic Fracture Toughness, London; PVRC/MPC Joint Task Group on Fracture Toughness Properties for Nuclear Components, Working Group on Instrumented Precracked Charpy Test, Chairman C. Buchalet, Westinghouse Nuclear Energy Systems (1974), "Recommended Procedure for Instrumented Precracked Charpy Testing;" Turner, C. E. (1975), "Dynamic Fracture Toughness Measurements by Instrumented Impact Testing," Advanced Seminar on Fracture Mechanics, Commission of the European Communities, Joint Research Centre, (Ispra, Italy) that the quasi static procedure can be applied only when the time to fracture $t_f$ of the specimen is longer than about three times the period $\tau$ of the characteristic oscillation of the impacted specimen:

$$t_f > 3\tau$$

The period $\tau$ is given approximately by the empirical formula (IIW (International Institute of Welding, Commission X)), U.K., Briefing Group on Dynamic Testing (1976), "Some Proposals for Dynamic Toughness Measurement," Proc. Int. Conf. Dynamic Fracture Toughness, London; Glover, A. P., F. A. Johnson, J. C. Radon, and C. E. Turner (1976), "Dynamic Fracture Toughness Measurement by Instrumented Bend Testing and Compact K Testing," Proc. Int. Conf. Dynamic Fracture Toughness, London; Matthews, W. T. (1970), "The Role of Impact Testing in Characterizing the Toughness of Materials," ASTM STP 466—*Impact Testing of Metals*, American Society for Testing and Materials, Philadelphia, pp. 3–20; Turner, C. E. (1970), "Measurement of Fracture Toughness by Instrumented Impact Test," ASTM STP 466—*Impact Testing of Metals*, American Society for Testing and Materials, Philadelphia, pp. 93–114

$$\tau = 1.68 \, (S \cdot W \cdot B \cdot C \cdot E^{\frac{1}{2}}/c_1)$$

where S is the support span, W and B are the width and the thickness of the specimen, C is the specimen compliance, E is Young's modulus and $c_1$ is the longitudinal wave speed. Short periods, therefore, result for small specimen dimensions. Long fracture times $t_f$, on the other hand, are obtained only when rather ductile materials are tested at low impact velocities. The condition (1) therefore restricts the applicability of impact tests in an unsatisfactory way:

Specimens of large dimensions, which are often required for a valid toughness test, cannot be utilized;
Materials which fail in a more brittle manner cannot be investigated;
The maximum allowable loading rate is limited.

SUMMARY OF THE INVENTION

It is the object of the present invention to provide a method of measuring the dynamic fracture toughness that does not have these restrictions. The method can be applied for all experimental test conditions, especially in the brittle fracture and high velocity impact range, as long as the usual conditions for small plastic zones at the crack tip in the specimen are fulfilled.

BRIEF DESCRIPTION OF THE DRAWINGS

An embodiment of the invention will now be described by way of example and with reference to the accompanying drawings in which:

FIG. 1 shows a schematic impact response curve for determining the dynamic fracture toughness;

FIG. 2 shows an experimental arrangement for representing the physical principle of the shadow optical method of caustics applied in reflection;

FIG. 3 is a section, taken in the vicinity of the crack tip, of a specimen;

FIG. 6 shows an impact response curve according to the dynamic stress intensity factors obtained, and FIG. 7 shows an oscillogram of a method of determining the time to fracture from load signals registered at the hammer (upper trace) and at the crack tip (lower trace).

DESCRIPTION OF THE PREFERRED EMBODIMENT

Figure 4:
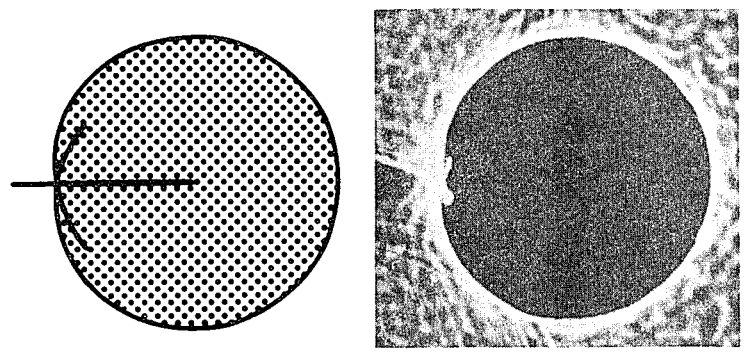
FIG. 4 shows a calculated shadow spot (left-hand side) and a measured shadow spot (right-hand side)

In previous investigations by some authors Kalthoff J. F., S. Winkler, W. Klemm, and J. Beinert (1979), "On the Validity of $K_{Id}$ Measurements in Instrumented Impact Tests," Proc. 5th Int. Conf. on Structural Mechanics in Reactor Technology, Berlin, Vol. G(4/6), North Holland Publishing Co.; Winkler, S., J. F. Kalthoff, and A. Gerscha (1979), "The Response of Pressure Vessel Steel Specimens on Drop Weight Loading," Proc. 5th Int. Conf. on Structural Mechanics in Reactor Technology, Berlin, Vol. G(4/6), North-Holland Publishing Company) the impact event was analyzed by performing experiments with prenotched bend specimens made from a model material and from steels. In addition to the load signal measured at the striking hammer, the dynamic stress intensity factor directly at the crack tip in the specimen was measured. In these experiments the gross test conditions were fixed, i.e. the same striking hammer, impact velocity, specimen material and specimen geometry were used, but the specific conditions for crack initiation, namely the notch tip acuity or the toughness of the material, were varied. In all the experiments, one unique curve for the stress intensity factor as a function of time, $K_I^{dyn}(t)$, was found. The critical stress intensity factors for onset of crack propagation were discrete values along this curve corresponding to the different times at which fracture initiation took place. The existence of such a behaviour was also considered by Loss (1975).

Based on these experimental findings, a measuring procedure is proposed for determining the dynamic fracture toughness values $K_{Id}$ for structural steels. The mechanical response of the specimen during impact is determined in pre-experiments. Utilizing the shadow optical method of caustics in reflection with an appropriate high strength steel, the dynamic stress intensity factor is established as a function of time, $K_I^{dyn}(t)$. This curve shown in FIG. 1 is called impact response curve.

The dynamic fracture toughness for a given construction material is then determined by performing an impact experiment and measuring the resulting time to fracture $t_f$. The dynamic fracture toughness value $K_{Id}$ is obtained (see FIG. 1) from the pre-established impact response curve and the measured time to fracture $t_f$ by the relation $$K_{Id} = K_I^{dyn}(t = t_f).$$

Stress intensity factors can be derived directly from the linear elastic stress strain field around the crack tip by means of the shadow optical method of caustics. This method, originally introduced by Manogg (1964) and later extended by Theocaris (1970), is an effective and simple experimental tool for determining stress intensity factors. It is particularly well suited for determining dynamic stress intensity factors when used in combination with high speed photography. The method has been successfully applied by Kalthoff et al. (Kalthoff, J. F., J. Beinert, and S. Winkler (1977), "Measurements of Dynamic Stress Intensity Factors for Fast Running and Arresting Cracks in Double-Cantilever-Beam Specimens," ASTM STP 627—*Fast Fracture and Crack Arrest,* American Society for Testing and Materials, Philadelphia, pp. 161-176; Kalthoff, J. F., J. Beinert, S. Winkler, and W. Klemm (1980), "Experimental Analysis of Dynamic Effects in Different Crack Arrest Test Specimens," ASTM STP 711—*Crack Arrest Methodology and Applications,* American Society for Testing and Materials, (Philadelphia) to dynamic fracture problems such as crack arrest and instability of cracks under impact and is used here for establishing the impact response curves.

The physical principle of the shadow optical method of caustics applied in reflection is shown in FIG. 2 representing an experimental arrangement. A steel specimen 3 having a mirrored surface 1 is provided with a notch 2. The mirrored surface 1 is illuminated by a light beam 4 from a light source 7. A load 9 is arranged to act upon the steel specimen 3. The steel specimen 3 is photographed by a camera 5 focussed on a virtual image plane 6 located behind the specimen. The steel specimen 3 rests on supports 10 relatively spaced in the longtiudinal direction of the specimen 3. A cross section through the specimen at the position of the crack tip is shown in FIG. 3. Due to the stress intensification at the crack tip, the thickness of the specimen is reduced in the area surrounding the crack tip. As a consequence, light near the crack tip is deflected towards the center line. An extension of the reflected light beams 8 onto the virtual image plane 6 at a distance $z_o$ behind the specimen results in a light configuration showing the crack tip as a dark shadow spot bounded by a region of bright light (the caustic).

The mode I shadow pattern was calculated by Manogg from the linear elastic stress strain field around the crack tip. FIG. 4 compares the result with the shadow pattern from a high strength steel specimen 3.

Quantitatively the diameter D of the caustic is a function of the stress intensity factor $K_I$ and is given by $$K_I = M \cdot D^{5/2} \text{ with } M = 9.34 \cdot 10^{-2} \frac{E}{\nu B z_o}$$

where
 D = Diameter of the caustic (for parallel light incident)
 E = Elastic modulus
 $\nu$ = Poisson's ratio
 B = Thickness of the plate
 $z_o$ = Distance between specimen and image plane.

Further experimental details of the technique are given by Beinert and Kalthoff (1980).

In order to apply the method of shadow patterns to steel and to determine stress intensity factors from the elastic stress-strain field in the vicinity of the tip of the crack, a steel with a sufficiently small plastic zone at the crack tip had to be utilized.

For this purpose bend specimens measuring 280 mm by 60 mm (10 mm thick) with initial notches of length $a_o = 20$ mm were machined from high-strength maraging steel X 2 NiCoMo 18 9 5 heat treated to a yield strength of $\tau_y = 2100$ MN/m$^2$ and a crack initiation toughness $K_{Id}$ of about 80 MN/m$^{3/2}$. This steel is produced by Stahlwerke Südwestfalen and designated HFX 760. Nominal composition: 18% Ni, 9% Co, 4.8% Mo and <0.03% C. Heat treatment: 480° C. for 4 hrs in air. The elastic modulus E and Poisson's ratio $\nu$ of this steel are about the same as those of usual structural steels. One side of the specimen was ground, lapped, and polished to achieve a highly planar and mirrored surface. The tip of the notch was blunted to increase the load carrying capacity of the specimen and thus allowed the impact response to be measured at stress intensity factors exceeding the fracture toughness of this steel. The specimens were tested on a support span of 240 mm in a DYNATUP 8100 drop weight tower. The mass of the striking hammer was 90 kg, the impact velocity was 5 m/s.

During the impact process shadow patterns at the tip of the crack were recorded with a Cranz Schardin 24 spark high speed camera. The distance $z_o$ between specimen and image plane was 1.5 m. The high speed camera was triggered by the sudden increase of the load signal registered by the strain gage on the hammer at the moment of contact with the specimen.

Figure 5:
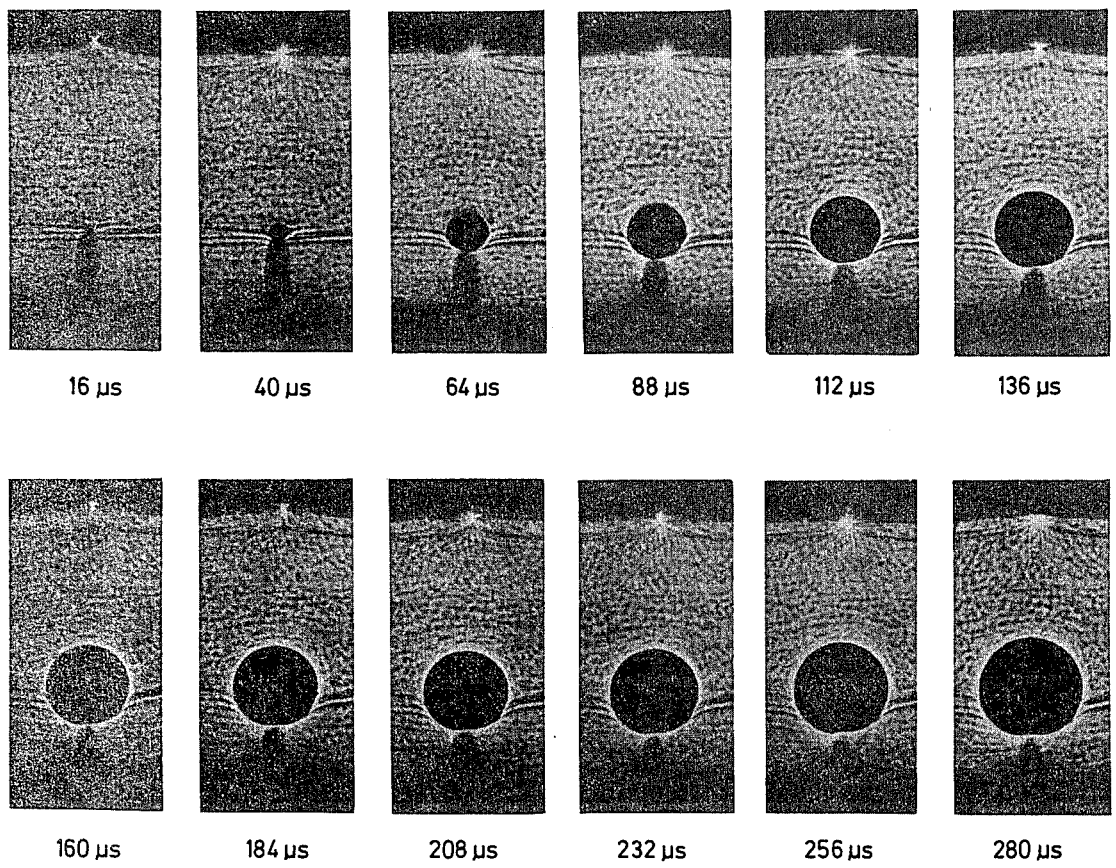
FIG. 5 shows a number of shadow optical photographs of the middle portion of a specimen during the impact event after the hammer contact, the time intervals being indicated.

A series of shadow optical pictures of the central part of the specimen taken during the impact event is given in FIG 5. Only 12 out of the total of 24 pictures are reproduced here. The time from the beginning of the impact process is indicated in each photograph.

Stress intensity factors obtained from such photographs are presented in FIG. 6. Data from several experiments performed under identical conditions are reproduced for times to 280 μs after impact. The nonlinear increase of the dynamic stress intensity factor with time is caused by dynamic effects in the specimen.

The $K_I^{dyn}(t)$-curve relates quantitatively to the response of the specimen to the impact event. The curve depends only on the elastic reaction of the specimen-impactor system, and therefore, is unique for the system considered and applies to all steel specimens of the same size tested under the same impact conditions. It is important to note that as a consequence this one relationship holds for steels of different toughnesses as long as the elastic properties of the steels, i.e. the constants E and $\nu$, are the same and the conditions for small plastic zones about the crack tip are fulfilled.

With the impact response curve established, the dynamic fracture toughness of a given steel is determined by measuring the time to fracture in an impact experiment.

The time to fracture of the specimen is obtained from signals of two uncalibrated strain gages, one of which is located on the peen of the hammer and the other on the specimen to the side of the crack tip. The leading edge of the signal from the hammer marks the beginning of the impact event. The onset of crack propagation, on the other hand, is indicated by the rapid drop in load registered by the crack tip strain gage. The records are electronically differentiated to give clear signals. The time to fracture $t_f$ is the interval between the two signals. A typical oscillogram for one experiment is shown in FIG. 7.

Time to fracture measurements in impact tests with steel specimens were performed to check the applicability of the concept of impact response curves for determining the dynamic fracture toughness $K_{Id}$. Specimens from two different structural steels, 30 CrNiMo 8 (nominal composition: 2.1% Cr, 1.9% Ni, 0.3% Mo and 0.27% C., water quenched and tempered. Yield strength $\sigma_y = 995$ MN/m$^2$, NDT-Temperature $= (+25°$ C.)) and 15 MnNi 63 (nominal composition: 1.6% Mn, 0.7% Ni and 0.17% C., heat treatment 530° C.-580° C. for about 1 h in air. Yield strength $\sigma_y = 360$ MN/m$^2$, NDT-Temperature $< -28°$ C. ($-55°$ C.)) were used for these investigations. Specimen dimensions, crack lengths, and impact conditions were identical to those used to obtain the impact response curve. However, sharp crack tips produced by fatigue loading according to ASTM E 399 were utilized in these fracture toughness tests. Each specimen was instrumented by a strain gage at a distance of 6 mm to the side of the crack tip. The time between this signal and the hammer signal, i.e. the time to fracture, was automatically recorded during the test by an electronic counter. The specimens were tested at different temperatures.

Time to fracture data from 4 experiments with 30 CrNiMo 8 specimens tested at temperatures of −80° C. and −60° C., and from 5 experiments with 15 MnNi 63 specimens tested at −110° C. and −80° C. are given in Table 1. The dynamic fracture toughness values $K_{Id}$ determined from the time to fracture values and from the impact response curve are given in the last column of Table 1. All experiments were performed in the brittle fracture range. The time to fracture $t_f$ is less than one period $\tau$ of the specimen oscillation (calculated from equation (2) to be 187 μs); thus condition (1) is not fulfilled and conventional measuring procedures would have failed. The crack tip loading rate $\dot{K}$ is of the order of $10^6$ MN·m$^{-3/2}$·s$^{-1}$. Tests at higher temperatures were not performed with these specimens because of minimum size requirements.

TABLE 1

Experimental Data

| Steel | Test Temperature T, °C. | Time to Fracture $t_f$ μs | Dynamic Fracture Toughness $K_{Id}$ MNm$^{-3/2}$ |
|---|---|---|---|
| 30 CrNiMo 8 | −82 | 73.5 | 57 |
|  | −80 | 80.5 | 68 |
|  | −80 | 74 | 58 |
|  | −60 | 83.5 | 72 |
| 15 MnNi 63 | −109 | 88 | (79) |
|  | −109 | 81 | 69 |
|  | −109 | 76 | 61 |
|  | −79 | 93.5 | 87 |
|  | −79 | 87 | 78 |

The method of determining the dynamic fracture toughness $K_{Id}$ according to the invention excels itself over the known measuring methods by various advantages. The impact response curves allow a fully dynamic evaluation of the test data. Kinetic effects are correctly taken into account for all times of the impact event. The method, therefore, can be applied for all experimental test conditions, in particular also in the small time to fracture range ($t_f < 3\tau$), i.e. when large specimens, high impact velocities, or brittle materials must be utilized. Even impact experiments at very high velocities, which exceed the velocities obtained by a pendulum or a drop weight, can be evaluated. Such high loading rates are of importance for the determination of real lower bound fracture toughness data, $K_{IR}(T)$, needed for a conservative design of structure and components with stringent safety requirements.

The proposed method does not require a calibrated instrumentation of the hammer which is usually needed in every impact experiment for determining the load at crack initiation. The present invention splits the measuring problem into two separate tasks: The determination of the impact response curve and the measurement of the time to fracture. The complicated determination of the impact response curve has to be carried out only once for a fixed experimental arrangement. A set of impact response curves for different experimental arrangements utilized in practice can be established. The actual $K_{Id}$-determination then requires only a relatively simple and inexpensive measurement of the time to fracture via uncalibrated instrumentations of the hammer and of the specimen.

Thus, an engineer in a test laboratory can determine the dynamic fracture toughness $K_{Id}$ for a certain steel by measuring only the time to fracture in an impact experiment and by utilizing that impact response curve which applies to the prevailing experimental conditions.

The invention may be embodied in other specific forms without departing from the spirit or essential characteristics thereof. The embodiment is therefore to be considered in all respects as illustrative and not restrictive.

What is claimed is:

1. A method of determining the impact fracture toughness $K_{Id}$ of construction materials by applying impact tests to bend specimens, each having a notch therein which is subsequently extended by loading said specimen to form an artificial crack therein, comprising the steps of:
    (a) determining according to the shadow optical method of caustics the impact response curve for a particular loading arrangement and specimen geometry;
    (b) measuring by an impact test the time to fracture $t_f$ of a corresponding specimen made of a material to be tested, and
    (c) ascertaining from the time to fracture with the aid of the impact response curve the impact fracture toughness $K_{Id}$ of the construction material of the bend specimen.

2. A method of determining the impact fracture toughness of structural steel as claimed in claim 1, wherein the impact response curve is determined with the aid of specimens of high-strength steel.

3. A method of determining the impact fracture toughness of structural steel as claimed in claim 1 wherein said impact test comprises striking said specimen with the peen of a hammer.

4. A method of determining the impact fracture toughness of structural steel as claimed in claim 3, wherein the time to fracture is obtained from signals of two uncalibrated strain gages, one of said gages being located on the peen of the hammer and the other on the specimen to the side of the crack tip.

5. A method of determining the impact fracture toughness of structural steel as claimed in claim 1 wherein said structural material is steel.

6. A method of determining the impact fracture toughness of structural steel as claimed in claim 1 wherein said structural material is a plastic material.

* * * * *